United States Patent
Chen et al.

(10) Patent No.: US 7,415,391 B2
(45) Date of Patent: Aug. 19, 2008

(54) COMPLEX EVENT EVALUATION SYSTEMS AND METHODS

(75) Inventors: Pin-Chan Chen, Taichung (TW); Jen-Feng Li, Taipei (TW); Wen-Ju Huang, Taipei (TW); Chih-Hao Hsu, Taipei (TW)

(73) Assignee: Institute for Information Industry, Taipei (TW)

( * ) Notice: Subject to any disclaimer, the term of this patent is extended or adjusted under 35 U.S.C. 154(b) by 0 days.

(21) Appl. No.: 11/641,703

(22) Filed: Dec. 20, 2006

(65) Prior Publication Data
US 2008/0114574 A1    May 15, 2008

(30) Foreign Application Priority Data
Nov. 9, 2006  (TW) .............................. 95141481 A

(51) Int. Cl.
*G06F 11/00* (2006.01)
(52) U.S. Cl. ............... 702/189; 709/220; 709/221; 709/222; 709/223; 709/224; 709/225; 714/4; 714/37; 714/47; 340/506
(58) Field of Classification Search .................. 702/189; 709/220–225; 714/4, 37, 47; 340/506
See application file for complete search history.

(56) References Cited

U.S. PATENT DOCUMENTS
7,213,068 B1 *   5/2007   Kohli et al. .................. 709/225

* cited by examiner

*Primary Examiner*—John E. Barlow, Jr.
*Assistant Examiner*—Sujoy K Kundu
(74) *Attorney, Agent, or Firm*—Birch, Stewart, Kolasch & Birch, LLP

(57) ABSTRACT

Complex event evaluation systems and methods are disclosed. A mathematics model for complex events and corresponding factors, and calculates a critical level of respective complex events according to weightings of respective factors in the mathematics model are provided. If several complex events occur simultaneously, a priority of respective complex events is calculated according to the historic occurrence of respective complex events. The critical level and priority of respective complex events are provided to users for decision making. Additionally, the mathematics model is established and adjusted according to the feedback scores for complex events.

15 Claims, 7 Drawing Sheets

COMPLEX EVENT EVALUATION SYSTEMS AND METHODS

BACKGROUND OF THE INVENTION

1. Field of the Invention

The disclosure relates generally to complex event evaluation systems and methods, and, more particularly to systems and methods that evaluate critical level and priority of respective complex events.

2. Description of the Related Art

In event management systems such as network or medical event management systems, the occurrence of respective simplex events is monitored, and respective simplex events are filtered according to specific system predefined criteria. For example, in patient clinical monitoring systems, life status factors such as body temperature, breath speed, blood pressure, blood urea nitrogen, red blood cells (RBC) in urine, microalbuminuria, and others of a respective patient are monitored. If a respective factor exceeds its predefined upper and/or lower thresholds, a simplex event corresponding to the factor occurs.

All simplex events conforming to corresponding criteria are aggregated to generate one or several new events, called complex events. U.S. Pat. No. 6,336,139 discloses an event detection and aggregation mechanism in a distributed computing environment. Several criteria such as matching, duplicate, pass through, reset and threshold rules are provided for filtering simplex events. If simplex events conform to at least one of the criteria, the conformant simplex events are aggregated to generate at least one complex event for further processing. For example, if the body temperature, blood pressure, blood urea nitrogen, and RBC in urine of a patient are high, the patient may have diabetes. If the blood pressure and microalbuminuria of a patient are high, the patient may have hypertension. In the described examples, diabetes and hypertension are complex events aggregated by various factors (simplex events).

In addition to the direct influence of the occurrence of respective simplex events to complex events, the degree of influence of respective simplex events on complex events may be different. Further, the occurrence situation of respective simplex events may also directly influence the critical level of complex events. However, in the conventional systems, the aggregated complex events do not show the degree of influence of respective simplex events. That is the critical level of respective complex events cannot be determined. For example, if several patients have diabetes, the conventional clinical patient monitoring systems are unable to distinguish the degree of patient danger. Additionally, the priority of respective complex events cannot be known. For example, if two patients have diabetes and hypertension respectively, the conventional patient clinical monitoring systems are unable to determine an optimal processing order for patients. Further, because of differences in the individual constitutions of respective patients, for example the blood pressure of some patients may be always high, conventional systems may produce unreliable or erroneous judgments.

BRIEF SUMMARY OF THE INVENTION

Complex event evaluation systems and methods are provided. The present invention provides a mathematics model for complex events and corresponding factors, and calculates a critical level of respective complex events according to weightings of respective factors in the mathematics model. If several complex events occur simultaneously, a priority of respective complex events is calculated according to the historic occurrence of respective complex events. The critical level and priority of respective complex events are provided to users for decision making. Additionally, the mathematics model is established and adjusted according to the feedback scores for complex events.

An embodiment of a complex event evaluation system comprises an event aggregation module, a weight calculation model, and a weight score calculation module. The event aggregation module receives a plurality of first events, each comprising at least one event value, and generates an event pool comprising at least one second event accordingly. The weight calculation model records a weight calculation function corresponding to the second event, where the weight calculation function comprises weightings corresponding to respective first events. The weight score calculation module calculates a weight score of the second event according to event values corresponding to respective first events and the weight calculation function corresponding to the second event, and evaluates a critical level of the second event according to the weight score of the second event.

In an embodiment of a complex event evaluation method, a plurality of first events, each comprising at least one event value is received. An event pool comprising at least one second event is generated according to the first events. A weight calculation model is provided. The weight calculation model records a weight calculation function corresponding to the second event, where the weight calculation function comprises weightings corresponding to respective first events. A weight score of the second event is calculated according to event values corresponding to respective first events and the weight calculation function corresponding to the second event. A critical level of the second event is evaluated according to the weight score of the second event.

Complex event evaluation systems and methods may take the form of program code embodied in a tangible media. When the program code is loaded into and executed by a machine, the device becomes an apparatus for practicing the disclosed method.

BRIEF DESCRIPTION OF THE DRAWINGS

The invention will become more fully understood by referring to the following detailed description with reference to the accompanying drawings, wherein.

DETAILED DESCRIPTION OF THE INVENTION

Complex event evaluation systems and methods are provided.

Figure 1:
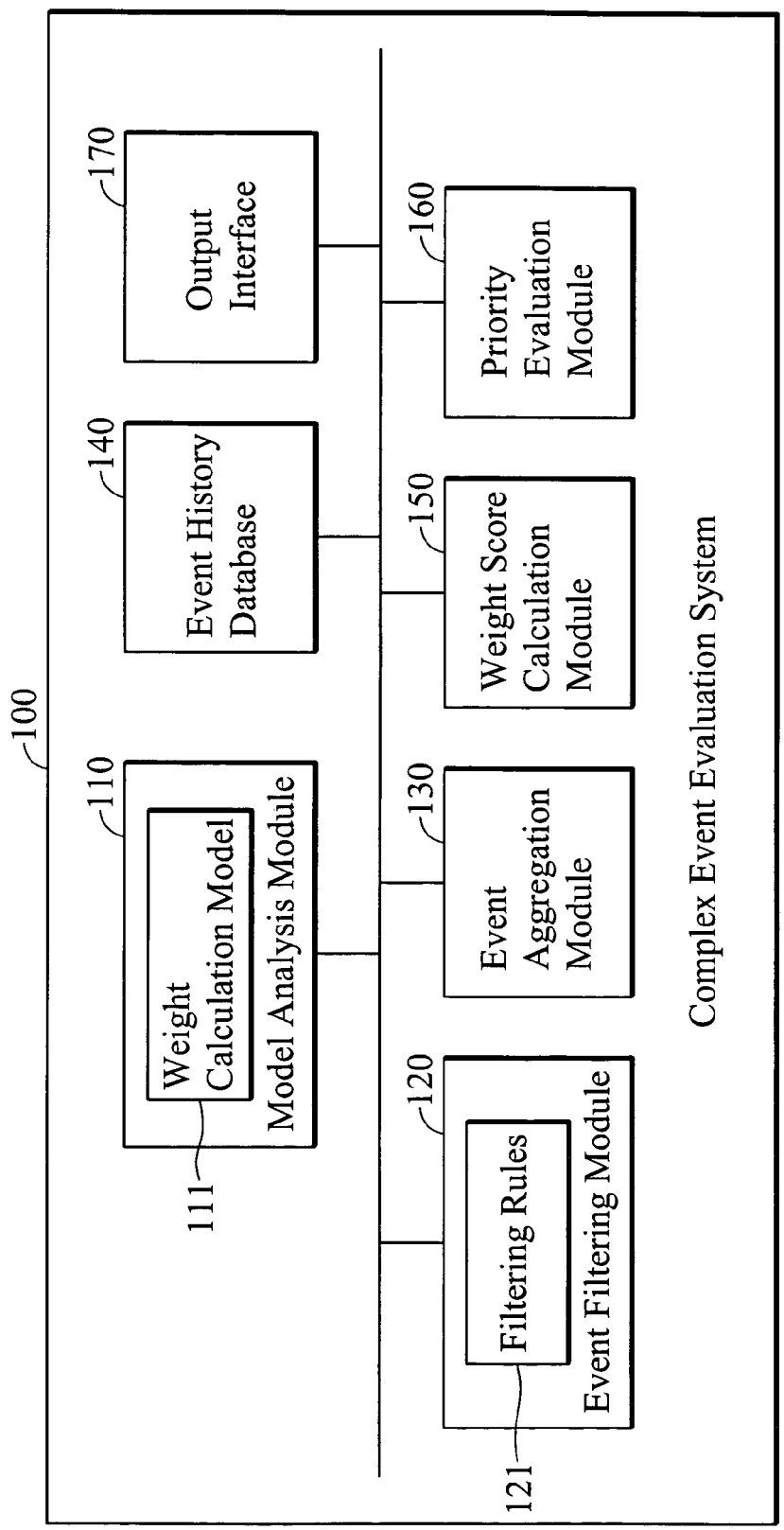
FIG. 1 is a schematic diagram illustrating an embodiment of a complex event evaluation system.

FIG. 1 illustrates an embodiment of a complex event evaluation system. The system 100 comprises a model analysis module 110, an event filtering module 120, an event aggregation module 130, an event history database 140, a weight score calculation module 150, a priority evaluation module 160, and an output interface 170.

The model analysis module 110 comprises at least one weight calculation model 111. The weight calculation model 111 may be a regression model, such as multiple regression, simple linear regression, and/or multi-variable regression models, and not limited thereto. The model analysis module 110 constructs the weight calculation model 111 by performing best-fit regression analysis based on data during event occurrence and scores provided by experts, such that the weight calculation model 111 to be regressed with optimal regression reliability. The weight calculation model 111 comprises a plurality of weight calculation functions corresponding to various complex events, where each weight calculation function comprises weightings corresponding to respective simplex events. For example, when simplex events A and B occur, complex events A and E are generated. Event values during each occurrence of simplex events A and B are provided to the model analysis module 110. Additionally, experts also provide scores during each occurrence of complex events A and E. The model analysis module 110 can calculate respective weight calculation functions corresponding to complex events A and E according to the weight calculation model 111, event values of simplex events A and B, and scores of complex events A and E. The weight calculation functions corresponding to complex events A and E record weightings corresponding to simplex events A and B. For example, the weight calculation function corresponding to complex event E may be $W_E = \alpha_1 X_1 + \alpha_2 X_2 + \epsilon$, where $W_E$ is a weight score of complex event E, $X_1$ and $X_2$ are event values of simplex events A and B, $\alpha_1$ and $\alpha_2$ are weightings corresponding to simplex events A and B, and $\epsilon$ is an adjustment constant. Therefore, when simplex events A and B occur, the weight score of complex event E can be obtained according to the event values corresponding to simplex events A and B. It is understood that the model analysis module 110 can continue to adjust the weight calculation model 111 according to new events as they occur.

Figure 2:
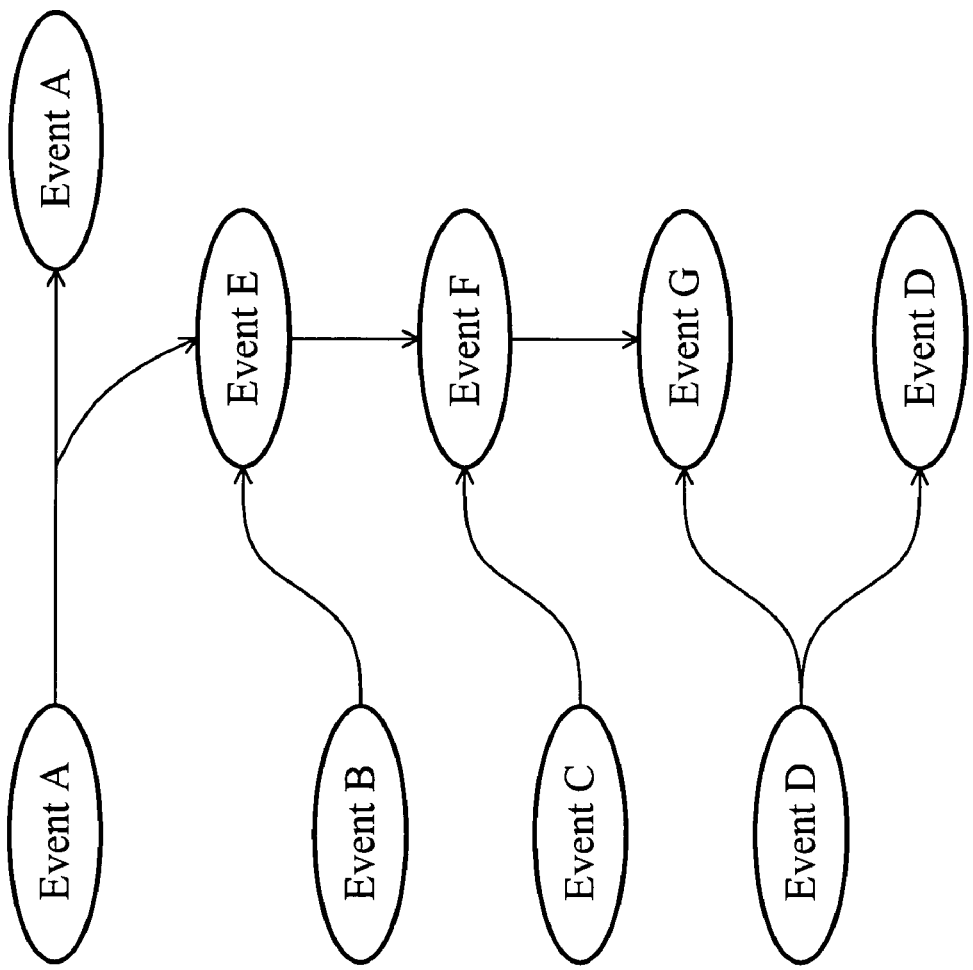
FIG. 2 is a schematic diagram illustrating an example of event aggregation.
Figure 3:
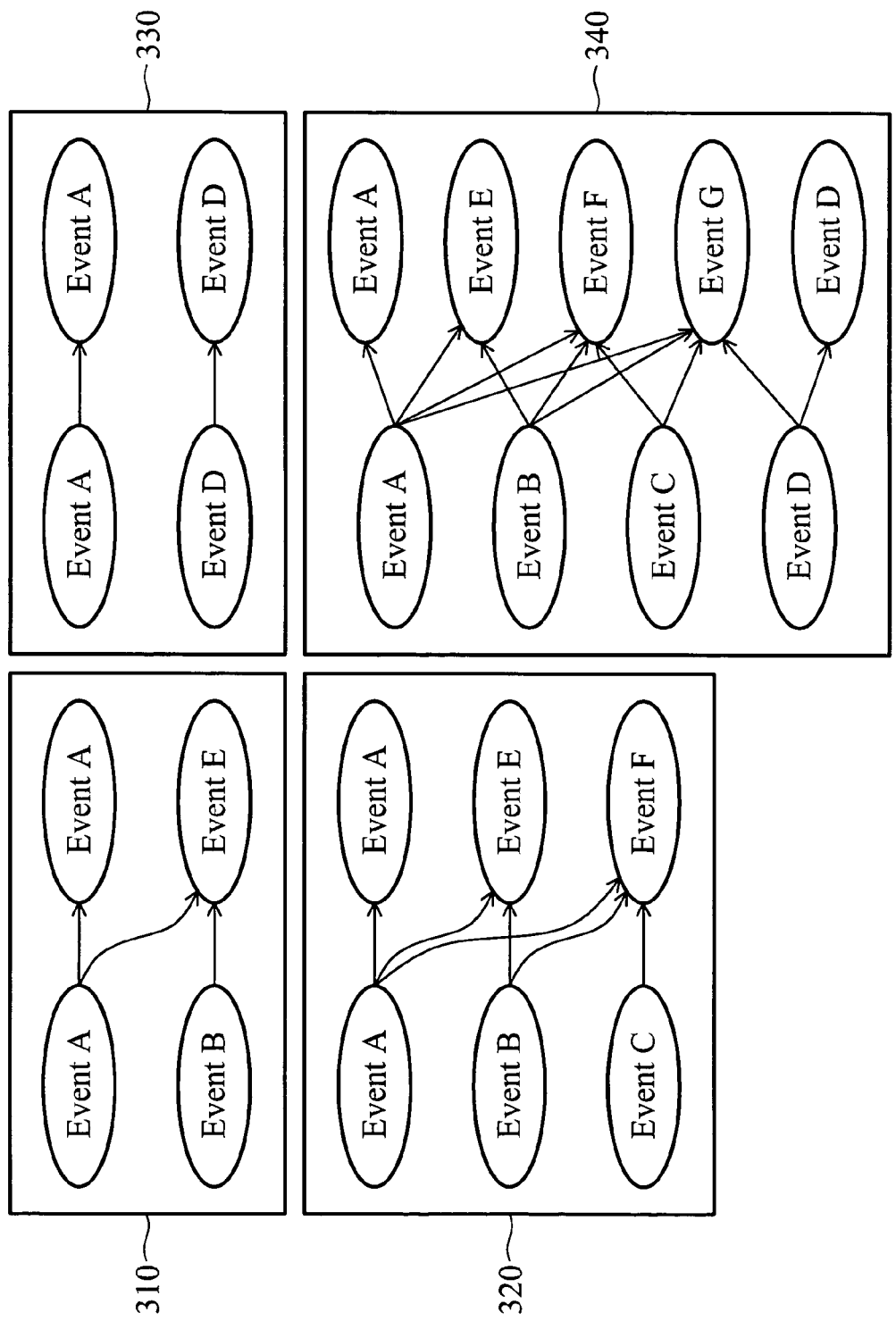
FIG. 3 is a schematic diagram illustrating an event pool corresponding to the event aggregation in FIG. 2.

The event filtering module 120 comprises filtering rules 121. When a simplex event occurs, the event filtering module 120 compares the simplex event with the filtering rules 121. If the simplex event simultaneously conforms to one or several of the filtering rules 121, the simplex event is passed to the event aggregation module 130. The filtering rules 121 can be set according to different requirements and environments. The event aggregation module 130 determines whether complex events should be generated according to the occurrence of simplex events. The event aggregation module 130 receives simplex events from the event filtering module 120, and generates an event pool comprising at least one complex event. FIG. 2 illustrates an example of event aggregation. As shown in FIG. 2, when event A occurs, event A is generated. When events A and B occur, events A and E are generated. When events A, B and C occur, events A, E and F are generated. When events A, B, C and D occur, events A, E, F, G and D are generated. When event D occurs, event D is generated. Note that a complex event may be at least one simplex event defined in another event pool. For example, when events A and B occur, events A and E are generated. When event C occurs with event E, events A, E and F are generated. Additionally, the above example comprises several event pools, such as event pools 310, 320, 330 and 340 in FIG. 3. When a specific event occurs, a specific event pool is selected for further processing.

Figure 4:
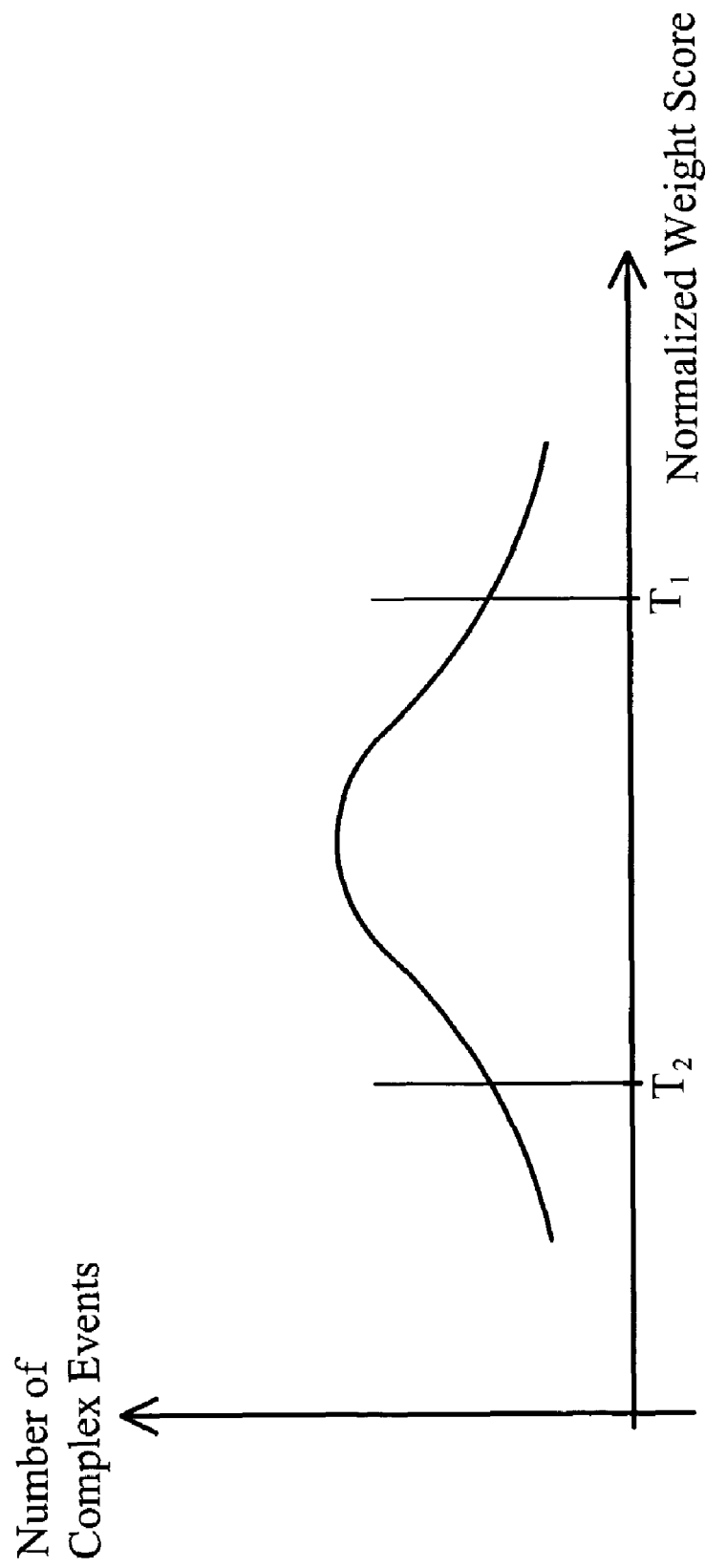
FIG. 4 is a schematic diagram illustrating an example of critical level distribution for complex events.
Figure 5:
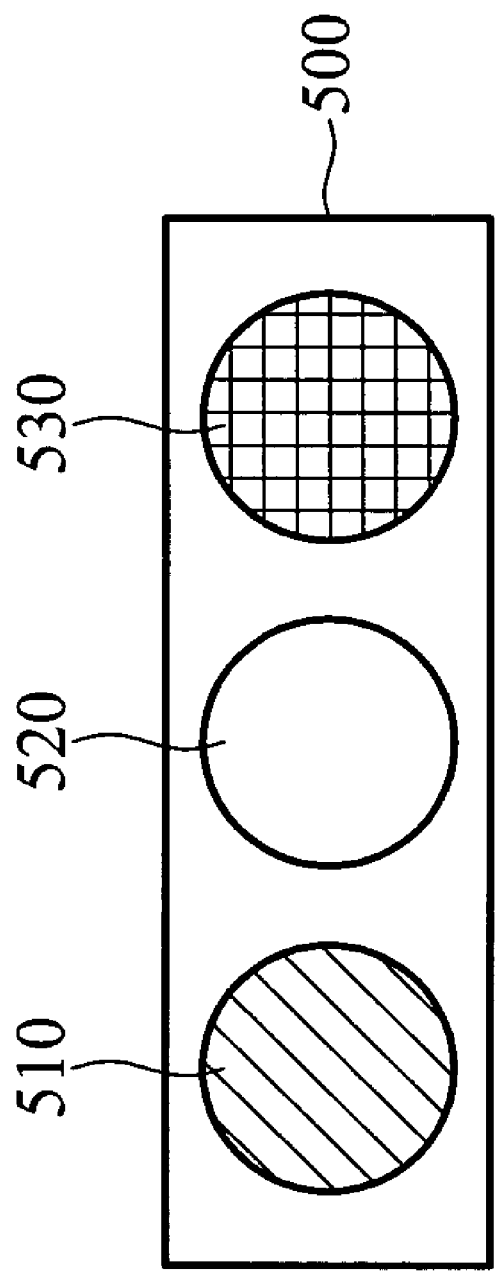
FIG. 5 is a schematic diagram illustrating lights corresponding to different critical levels.
Figure 6:
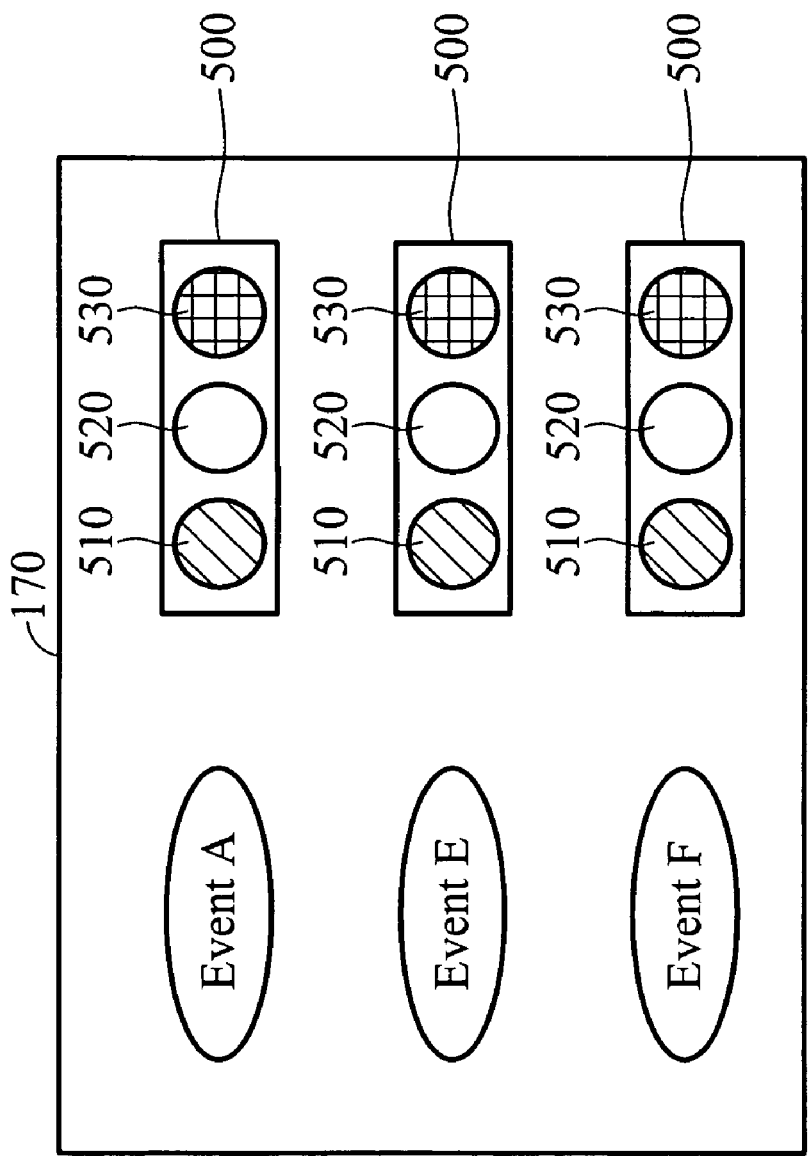
FIG. 6 is a schematic diagram illustrating an example of an output interface.

The event history database 140 records historic simplex events, event values corresponding to the simplex events, complex events corresponding to the simplex events and weight scores of the complex events. The weight score calculation module 150 calculates a weight score of a complex event according to event values corresponding to respective simplex events generating the complex event and a weight calculation function for the complex event. After the weight score is calculated, the weight score calculation module 150 evaluates a critical level of the complex event according to the weight score of the complex event. In some embodiments, the weight score calculation module 150 retrieves the weight scores of the historic complex events from the event history database 140, and normalizes the weight score of the complex event accordingly to obtain a normalized weight score of the complex event. The weight score calculation module 150 compares the normalized weight score with at least one predefined threshold to obtain the critical level of the complex event. It is understood that the number of critical levels and predefined thresholds can be set according to different requirements and environments. FIG. 4 illustrates an example of critical level distribution for complex events. In FIG. 4, if the normalized weight score exceeds threshold T1, the critical level of the complex event is highest. If the normalized weight score exceeds threshold T2 but less than threshold T1, the critical level of the complex event is middle. If the normalized weight score is less than threshold T2, the critical level of the complex event is lowest. The output interface 170 may be a graphical interface. In some embodiments, different critical levels may correspond to different lights 400, as shown in FIG. 5. For example, if the critical level is highest, light 530, for example, a red light, is illuminated. If the critical level is middle, light 520, for example, a yellow light is on. If the critical level is lowest, light 510, for example, a green light, is illuminated. The weight score calculation module 150 determines a light according to the critical level of complex event, and displays the light in the output interface 170, as shown in FIG. 6. In the example of FIG. 6, events A, E and F have respective lights, representing the critical levels thereof.

The priority evaluation module 160 can analyze the processing order for complex events. The priority evaluation module 160 retrieves historic occurrence probability of respective complex events under the occurrence of a selected event pool from the event history database 140. The priority evaluation module 160 calculates a priority of a complex event according to the historic occurrence probability and the normalized weight score of the complex event. For example, if the normalized weight score of event E is $NW_E$, the historic occurrence probability of event E is $P_E$, the priority of event E is $P_{rE} = P_E \times NW_E$. The priority evaluation module 160 sorts complex events according to its corresponding priority, thereby determining the processing order for the complex events.

Figure 7:
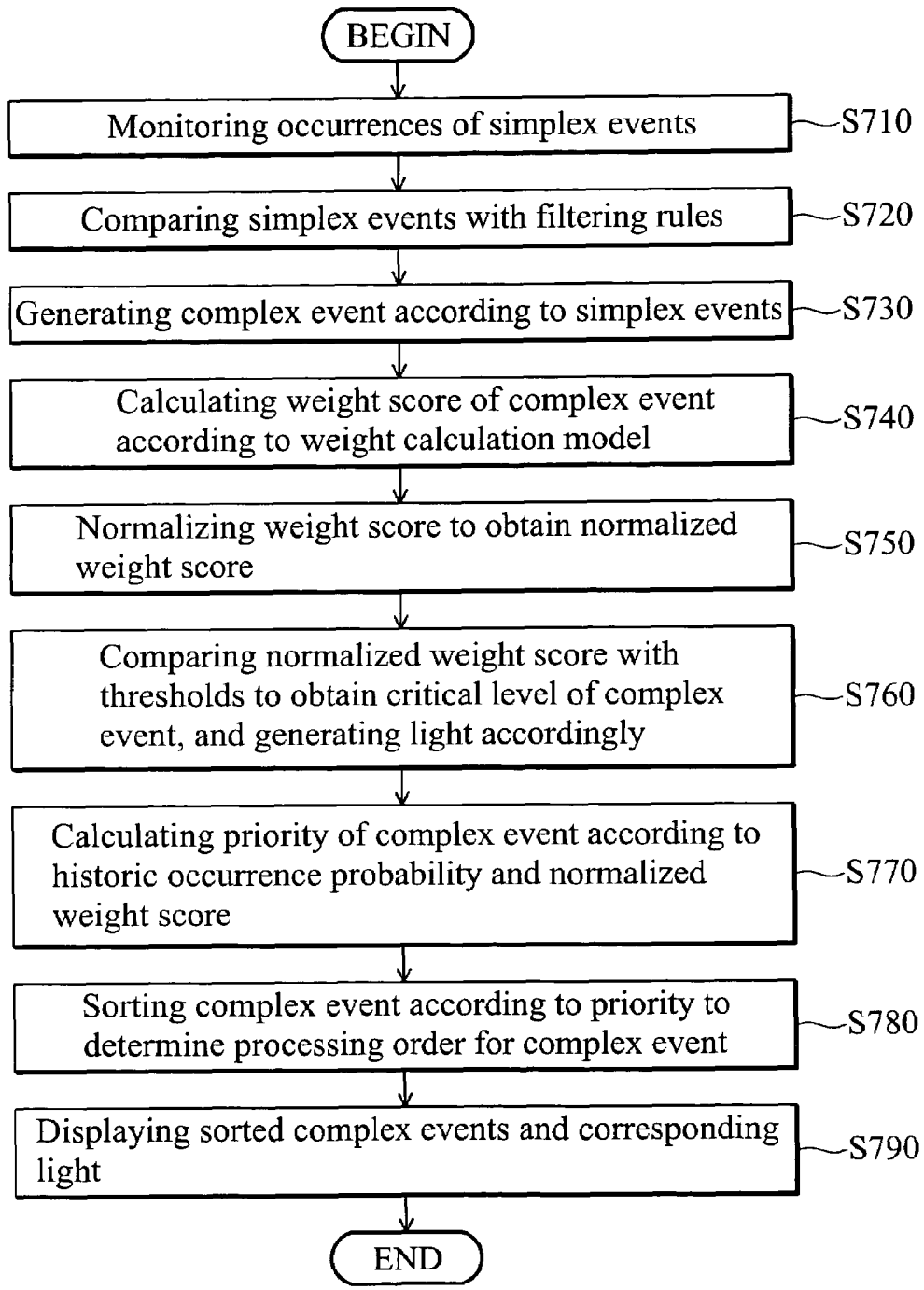
FIG. 7 is a flowchart of an embodiment of a complex event evaluation method.

FIG. 7 is a flowchart of an embodiment of a complex event evaluation method.

In step S710, the occurrences of respective simplex events are monitored. In step S720, respective simplex events are compared with filtering rules. If the simplex events conform to the filtering rules, in step S730, an event pool comprising at least one complex event is generated according to the simplex events. In step S740, a weight score of the at least one complex event is calculated according to event values corresponding to respective simplex events and the weight calculation function corresponding to the complex event. After the weight score is calculated, in step S750, the weight score of the complex event is normalized according to the weight scores of the historic complex event to obtain a normalized weight score of the complex event. In step S760, the normalized weight score is compared with predefined thresholds to obtain the critical level of the complex event, and generates a light according to the critical level. In step S770, a priority of the complex event is calculated according to the historic occurrence probability under the occurrence of the event pool and the normalized weight score of the complex event, and in step S780, the at least one complex event is sorted according to its corresponding priority to determine the processing order for the at least one complex event. In step S790, the sorted complex event and the corresponding light are displayed to inform users. Users can select a specific complex event for process according to the order of the at least one complex event and the light representing critical level.

Accordingly, the invention provides a mathematics model for complex events and corresponding factors, and calculates a critical level of respective complex events according to weightings of respective factors in the mathematics model. If several complex events occur simultaneously, a priority of respective complex events is calculated according to the historic occurrence of respective complex events. The critical level and priority of respective complex events are provided to users for decision making. Additionally, the mathematics model is established and adjusted according to the feedback scores for complex events.

Complex event evaluation systems and methods, or certain aspects or portions thereof, may take the form of program code (i.e., executable instructions) embodied in tangible media, such as floppy diskettes, CD-ROMS, hard drives, or any other machine-readable storage medium, wherein, when the program code is loaded into and executed by a machine, such as a computer, the device thereby becomes an apparatus for practicing the methods. The methods may also be embodied in the form of program code transmitted over some transmission medium, such as electrical wiring or cabling, through fiber optics, or via any other form of transmission, wherein, when the program code is received and loaded into and executed by a machine, such as a computer, the device becomes an apparatus for practicing the disclosed methods. When implemented on a general-purpose processor, the program code combines with the processor to provide a unique apparatus that operates analogously to application specific logic circuits.

While the invention has been described by way of example and in terms of preferred embodiment, it is to be understood that the invention is not limited thereto. Those who are skilled in this technology can still make various alterations and modifications without departing from the scope and spirit of this invention. Therefore, the scope of the invention shall be defined and protected by the following claims and their equivalents.

What is claimed is:

1. A complex event evaluation system, comprising:
an event aggregation module receiving a plurality of first events, each comprising at least one event value, and generating an event pool comprising at least one second event according to the first events;
a weight calculation model comprising a weight calculation function corresponding to the at least one second event, where the weight calculation function comprises weightings corresponding to respective first events; and
a weight score calculation module calculating a weight score of the at least one second event according to the event values corresponding to respective first events and the weight calculation function corresponding to the at least one second event, evaluating a critical level of the at least one second event according to the weight score of the at least one second event retrieving the weight scores of the historic events of the at least one second events from the event history database, normalizing the weight score of the at least one second event accordingly to obtain a normalized weight score of the at least one second event, and comparing the normalized weight score with at least one predefined threshold to obtain the critical level of the at least one second event.

2. The system of claim 1 wherein the weight score calculation module further determines a light according to the critical level of the at least one second event, and displays the light in a graphic interface.

3. The system of claim 1 further comprising a priority evaluation module retrieving historic occurrence probability of the at least one second event under the occurrence of the event pool from the event history database, calculating a priority of the at least one second event according to the historic occurrence probability and the normalized weight score of the at least one second event, and determines a processing order for the at least one second event according to the priority thereof.

4. The system of claim 1 further comprising an event filtering module comparing the first events with at least one filtering rule, and outputting the first events to the event aggregation module if the first events conform to the filtering rule.

5. The system of claim 1 wherein the weight calculation model comprises at least one regression model.

6. A complex event evaluation method, comprising:
receiving a plurality of first events, each comprising at least one event value;
generating an event pool comprising at least one second event according to the first events;
providing a weight calculation model comprising a weight calculation function corresponding to the at least one second event, where the weight calculation function comprises weightings corresponding to respective first events;
calculating a weight score of the at least one second event according to the event values corresponding to respective first events and the weight calculation function corresponding to the at least one second event;
evaluating a critical level of the at least one second event according to the weight score of the at least one second event;
retrieving the weight scores of the historic events of the at least one second event from an event history database;
normalizing the weight score of the at least one second event accordingly to obtain a normalized weight score of the at least one second event; and
comparing the normalized weight score with at least one predefined threshold to obtain the critical level of the at least one second event.

7. The method of claim 6 further comprising:
determining a light according to the critical level of the at least one second event; and
displaying the light in a graphic interface.

8. The method of claim 6 further comprising:
retrieving historic occurrence probability of the at least one second event under the occurrence of the event pool from the event history database;
calculating a priority of the at least one second event according to the historic occurrence probability and the normalized weight score of the at least one second event; and
determines a processing order for the at least one second event according to the priority thereof.

9. The method of claim 6 further comprising:
comparing the first events with at least one filtering rule; and outputting the first events to the event aggregation module if the first events conform to the filtering rule.

10. The method of claim 6 wherein the weight calculation model comprises at least one regression model.

11. A machine-readable storage medium comprising a computer program, which, when executed, causes a device to perform a complex event evaluation method, the method comprising:

receiving a plurality of first events, each comprising at least one event value;

generating an event pool comprising at least one second event according to the first events;

providing a weight calculation model comprising a weight calculation function corresponding to the at least one second event, where the weight calculation function comprises weightings corresponding to respective first events;

calculating a weight score of the at least one second event according to the event values corresponding to respective first events and the weight calculation function corresponding to the at least one second event; and evaluating a critical level of the at least one second event according to the weight score of the at least one second event;

retrieving the weight scores of the historic events of the at least one second events from an event history database;

normalizing the weight score of the at least one second event accordingly to obtain a normalized weight score of the at least one second event; and comparing the normalized weight score with at least one predefined threshold to obtain the critical level of the at least one second event.

12. The storage medium of claim 11 wherein the method further comprises:

determining a light according to the critical level of the at least one second event; and displaying the light in a graphic interface.

13. The storage medium of claim 11 wherein the method further comprises:

retrieving historic occurrence probability of the at least one second event under the occurrence of the event pool from the event history database;

calculating a priority of the at least one second event according to the historic occurrence probability and the normalized weight score of the at least one second event; and determines a processing order for the at least one second event according to the priority thereof.

14. The storage medium of claim 11 wherein the method further comprises:

comparing the first events with at least one filtering rule; and outputting the first events to the event aggregation module if the first events conform to the filtering rule.

15. The storage medium of claim 11 wherein the weight calculation model comprises at least one regression model.

* * * * *